United States Patent
Onda et al.

(10) Patent No.: US 8,232,433 B2
(45) Date of Patent: Jul. 31, 2012

(54) CATALYST AND ALCOHOL SYNTHESIS METHOD

(75) Inventors: Ayumu Onda, Kochi (JP); Shuhei Ogo, Kochi (JP); Kazumichi Yanagisawa, Kochi (JP)

(73) Assignees: Kabushiki Kaisha Sangi, Tokyo (JP); Kochi University, Kochi (JP)

( * ) Notice: Subject to any disclaimer, the term of this patent is extended or adjusted under 35 U.S.C. 154(b) by 93 days.

(21) Appl. No.: 12/602,885

(22) PCT Filed: Aug. 17, 2009

(86) PCT No.: PCT/JP2009/003907
§ 371 (c)(1),
(2), (4) Date: Jan. 26, 2010

(87) PCT Pub. No.: WO2011/021232
PCT Pub. Date: Feb. 24, 2011

(65) Prior Publication Data
US 2011/0190553 A1     Aug. 4, 2011

(51) Int. Cl.
*C07C 29/32*    (2006.01)
*B01J 23/00*    (2006.01)

(52) U.S. Cl. .................................. 568/902.2; 502/340

(58) Field of Classification Search ............... 568/902.2; 502/340
See application file for complete search history.

(56) References Cited

U.S. PATENT DOCUMENTS
5,304,577 A * 4/1994 Nagata et al. ................. 524/417

FOREIGN PATENT DOCUMENTS
| JP | 11-217343 A | 8/1999 |
| JP | 2006022253 A | 1/2006 |
| WO | 9938822 A1 | 8/1999 |
| WO | 2006/059729 A1 | 6/2006 |

OTHER PUBLICATIONS

Ogo et al.; Synthesis of 1-Butanol from Ethanol over Substituted Hydroxyapatite Catalysts; 102nd Catalyst Discussion Meeting # Discussion Meeting A Abstracts, Sep. 23, 2008; 2 pages.

Tsuchida, T., et al., Direct Synthesis of n-Butanol from Ethanol over Nonstoichiometric Hydroxyapatite, Industrial and Engineering Chemical Research, Oct. 31, 2006, vol. 45, pp. 8634-8642.

* cited by examiner

*Primary Examiner* — Sikarl Witherspoon
(74) *Attorney, Agent, or Firm* — Hodgson Russ LLP

(57) ABSTRACT

The present invention is intended to provide a catalyst which is for synthesizing butanol from ethanol at a high selectivity and which comprises strontium phosphate apatite having the Sr/P atomic ratio of 1.5-2.0, and the synthesis method.

10 Claims, 2 Drawing Sheets

CATALYST AND ALCOHOL SYNTHESIS METHOD

TECHNICAL FIELD

The present invention relates to a catalyst for alcohol synthesis and an alcohol synthesis method. More particularly, the present invention relates to a catalyst for synthesizing butanol from ethanol, comprising strontium phosphate apatite having a specific Sr/P atomic ratio, and an alcohol synthesis method using the catalyst.

BACKGROUND ART

Recently, carbon-neutral biofuels are attracting attention as a global warming countermeasure. Among such biofuels, bioethanol is particularly attracting attention. Bioethanol is sometimes used directly as an alternative for gasoline, but is usually used by being mixed with petroleum gasoline. However, there is one drawback, in that phase separation easily happens when ethanol and gasoline are mixed. A solution for this is the use of alcohols such as butanol, which have larger carbon numbers than ethanol and which can be easily mixed with gasoline (being resistant to phase separation). But methods for obtaining butanol from biological resources are limited. In other words, methods for obtaining ethanol comprising fermenting a starch from sources such as corn and potatoes or sugar obtained from a source such as sugarcane by using enzymes have been established to a certain degree, but enzymes for efficiently producing butanol by fermentation have been unknown.

In view of the above, the present invention relates to a technique that was developed based on the conception of obtaining biobutanol by conversion of the obtained bioethanol to butanol by using a catalyst. On the other hand, there is a similar technique for obtaining acetaldehyde, butadiene, 1-butanol, high-octane fuels, and mixtures thereof from ethanol by a gas-phase reaction process using calcium phosphate apatite (Patent Documents 1 and 2).

However, even when these methods are applied to such purpose as above, the butanol selectivity is still unsatisfactory for industrialization purposes and a method for synthesizing butanol from ethanol at a higher selectivity was desired.

[Patent document 1] Japanese Laid-Open Patent Application No. 11-217343
[Patent document 2] WO2006/059729A1

DISCLOSURE OF THE INVENTION

Object to be Solved by the Invention

The object of the present invention is to provide a catalyst for synthesizing butanol from ethanol at a high selectivity and a butanol synthesis method.

Means to Solve the Object

Under the circumstances above, the present inventors made a keen study and focused on strontium phosphate apatite, then found it to be a catalyst with particularly superior butanol selectivity when used for the direct synthesis of butanol from ethanol. The present invention was thus completed. The present inventors have announced these results at the 102th Catalyst Discussion Meeting held on Sep. 23 to 26, 2008 (see Discussion Meeting A Abstracts "3H10 Synthesis of 1-Butanol from Ethanol over Substituted Hydroxyapatite Catalysts (Kochi University) ○Shuhei Ogo, Ayumu Onda, Kazumichi Yanagisawa").

The present invention relates to (1) to (7) as follows.
(1) A catalyst for synthesizing butanol from ethanol, wherein the catalyst comprises strontium phosphate apatite having a Sr/P atomic ratio of 1.5-2.0;
(2) The catalyst according to (1), wherein the Sr/P atomic ratio is 1.60-1.75;
(3) The catalyst according to (1) or (2), wherein the strontium phosphate apatite is $Sr_{10}(PO_4)_6(OH)_2$;
(4) An alcohol synthesis method for synthesizing butanol from ethanol, wherein the method comprises a step of contacting ethanol with the catalyst according to any one of (1) to (3);
(5) An alcohol synthesis method, wherein the method comprises a step of sequentially or intermittently removing to the outside of a reaction system at least butanol from a reaction product obtained by contacting ethanol with the catalyst according to any one of (1) to (3) and comprising butanol as a major component;
(6) The alcohol synthesis method according to (4) or (5), wherein ethanol is contacted with the catalyst at 200-350° C.; and
(7) The alcohol synthesis method according to any one of (4) to (6), wherein ethanol is produced using biomass as a material and the water content of the ethanol is 10% or less.

Effect of the Invention

The method of the present invention using a catalyst of the present invention enables synthesis of butanol from ethanol at a high selectivity.

BEST MODE OF CARRYING OUT THE INVENTION

Figure 1:
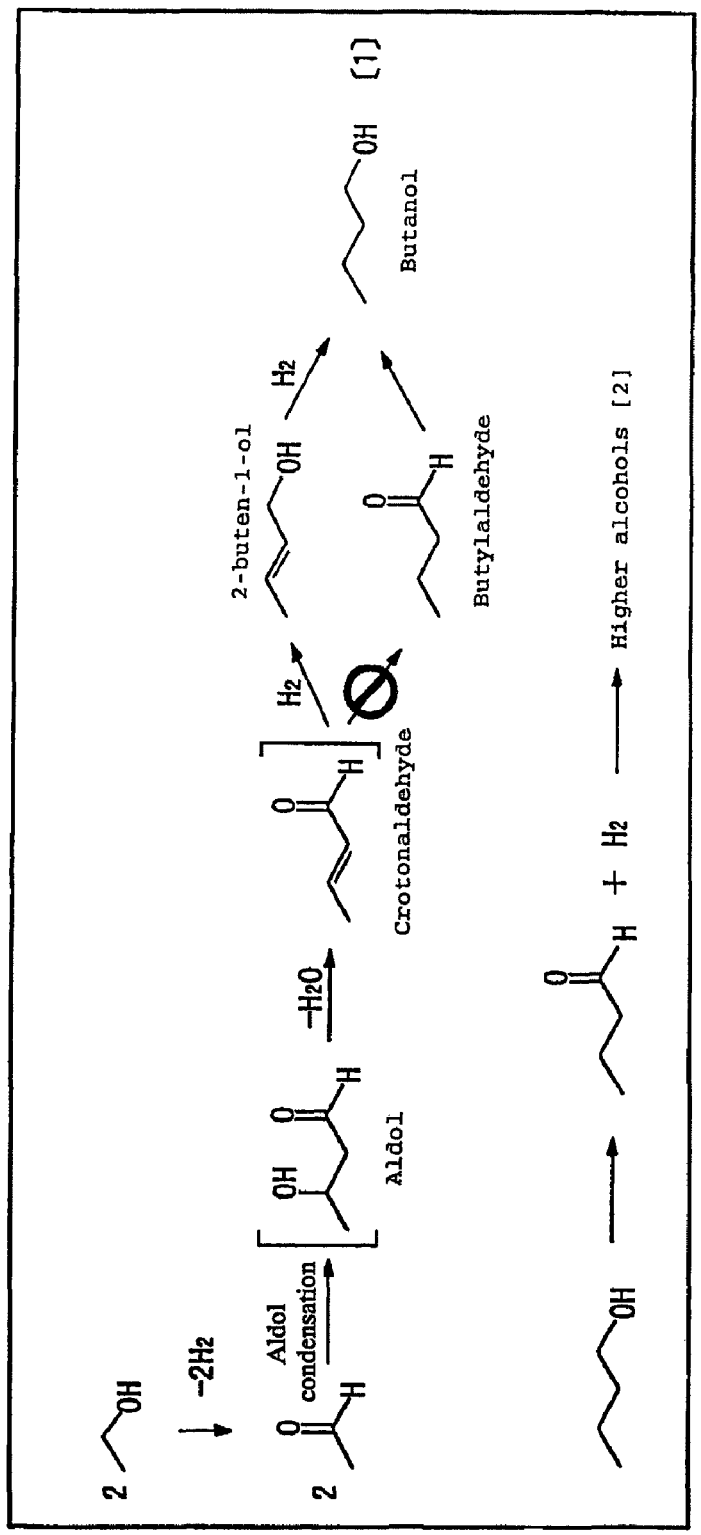
FIG. 1 is a reaction scheme showing the mechanism of butanol formation.

The present invention is explained in detail in the following.
1) The Sr/P atomic ratio is 1.5 to 2.0, preferably 1.60 to 1.75, where the representative example is $Sr_{10}(PO_4)_6(OH)_2$. Butanol selectivity or butanol yield might be decreased when the Sr/P atomic ratio is outside this range.
2) Butanol selectivity or butanol yield might be decreased when an apatite compound other than strontium phosphate apatite is used.
3) Strontium phosphate apatite having the Sr/P atomic ratio of 1.6 to 1.7 described in the above-mentioned (1) or (2) is preferred.
4) The specific surface area of an apatite compound is 0.5 $m^2$/g or more, preferably 10 $m^2$/g or more, from the viewpoint that this is especially effective for improving the yield.

Butanol referred to in the present invention mainly denotes n-butanol.

In the present invention, an apatite compound used as a catalyst comprises strontium phosphate apatite as a major component and may comprise various apatite compounds such as calcium phosphate apatite.

Strontium phosphate apatite includes solid solution and is represented by the general formula $Sr_{10-\alpha}M_{\alpha}(PO_4)_{6-\beta}(ZO_4)_{\beta}X_2$ [wherein M represents Ba, Ca, Mg, Pb, Cd, Fe, Co, Ni, Cu, Zn, La, H, etc., Z represents V, As, etc. (including a case where $CO_3$ is used in place of $(ZO_4)$), and X represents OH, F, Cl, etc.]. Usually, zero (0) is applied for both $\alpha$ and $\beta$, in which case the formula is, for example, $Sr_{10}(PO_4)_6(OH)_2$ and Sr/P=1.67.

A production method for apatite compounds is not particularly limited and known synthesis methods such as a hydrothermal synthesis, dry solid phase reaction, and wet precipitation reaction may be employed.

Further, the Sr/P molar ratio may be appropriately varied when preparing a strontium phosphate apatite compound. For example, an aqueous phosphate solution which has been made basic with NaOH (concentration of about 0.01-2M, preferably 0.05-0.5 M) is mixed with an aqueous strontium salt solution (concentration of about 0.01-3M, preferably 0.08-0.8 M), the resultant suspension is placed into an autoclave for a hydrothermal treatment at about 50-300° C., preferably 100-200° C., and at a pressure of about $1\times10^5$–$1\times10^7$ Pa, preferably $1\times10^5$–$2\times10^6$ Pa, then washed and dried for use. Depending on the composition and purpose of the catalyst, the amount of strontium salt and phosphate for use in a catalytic synthesis is adjusted to render the Sr/P molar ratio of 1.5-2.0, preferably 1.6-1.75.

Examples of the strontium salt for use include $Sr(NO_3)_2$ and examples of the phosphate for use include diphosphorus pentaoxide ($P_2O_5$). The Sr/P molar ratio of an apatite compound is controlled either by adjusting the ratio of strontium salt and phosphate or by adjusting the concentration of alkali to be added for synthesis.

For example, when $Sr(NO_3)_2$ and $P_2O_5$ are used as starting materials, an apatite compound is formed by rendering the alkaline concentration higher than 3 in terms of the OH/P molar ratio. Usually, strong alkali such as sodium hydroxide and potassium hydroxide is used, and the alkaline concentration is adjusted to 3.5-14 in terms of the OH/P molar ratio.

An apatite compound used as a catalyst in the present invention may be carried by a support such as alumina.

To produce butanol from ethanol by using a catalyst for alcohol synthesis of the present invention, wherein the catalyst comprises as a major component strontium phosphate apatite having physical properties as described above, ethanol and the catalyst may be brought into contact at an appropriate temperature. The temperature is preferably 200-350° C., and 250-300° C. is particularly preferred to increase butanol selectivity. When setting the temperature at 200° C. or higher, ethanol conversion rate is increased, and when setting the temperature at 350° C. or lower, side reactions (e.g., formation of higher alcohol, hydrocarbon, etc.) are inhibited and the decrease in butanol selectivity can be prevented.

Butanol yield can be increased by removing butanol and higher alcohol by-products from the mixture of reactant (ethanol) and products, which comprise butanol as a major component, during the reaction of ethanol using strontium phosphate apatite.

Further, a high concentration of butanol can be obtained by separating butanol at the latter stage of the reactor, and the material utilization rate of ethanol can be increased by recycling ethanol.

EXAMPLES

The present invention is explained in more detail in the following with reference to the Examples, while the present invention shall not be limited to these Examples.

(Preparation of Samples)

A catalyst of the present invention and a comparative catalyst were synthesized as follows.

(1) Preparation of a Comparative Catalyst [Sample (1)]

0.142 g of diphosphorus pentaoxide ($P_2O_5$) was dissolved at room temperature in a 1M aqueous solution of sodium hydroxide (7 ml) prepared at room temperature. To this resultant solution, 0.789 g of calcium nitrate ($Ca(NO_3)_2.4H_2O$) dissolved in an 8 mL aqueous solution was added to render the Ca/P ratio of 1.67, and a suspension was obtained.

The obtained suspension was introduced into an autoclave lined with Teflon® and subjected to a hydrothermal treatment at 110° C. for 14 hours under stirring. Pressure in the autoclave during the treatment was $1\times10^5$–$2\times10^5$ Pa. The suspension was subsequently taken out from the autoclave, centrifuged, washed with water, dried at 60° C., and a powdery catalytic composition (Ca—P) for comparison containing Ca and $PO_4$ was obtained.

(2) Preparation of a Catalyst of the Present Invention [Sample (2)]

0.142 g of diphosphorus pentaoxide ($P_2O_5$) was dissolved at room temperature in a 1M aqueous solution of sodium hydroxide (7 ml) prepared at room temperature. To this resultant solution, 0.706 g of strontium nitrate ($Sr(NO_3)_2$) dissolved in an 8 mL aqueous solution was added to render the Sr/P ratio of 1.67, and a suspension was obtained.

The obtained suspension was introduced into an autoclave lined with Teflon® and subjected to a hydrothermal treatment at 110° C. for 14 hours under stirring. Pressure in the autoclave during the treatment was $1\times10^5$–$2\times10^5$ Pa. The suspension was subsequently taken out from the autoclave, centrifuged, washed with water, dried at 60° C., and a powdery catalytic composition (Sr—P) containing Sr and $PO_4$ was obtained.

(3) Preparation of a Comparative Catalyst [Sample (3)]

0.142 g of diphosphorus pentaoxide ($P_2O_5$) was dissolved at room temperature in a 1M aqueous solution of sodium hydroxide (7 ml) prepared at room temperature. To this resultant solution, 1.105 g of lead nitrate ($Pb(NO_3)_2$) dissolved in an 8 mL aqueous solution was added to render the Pb/P ratio of 1.67, and a suspension was obtained.

The obtained suspension was introduced into an autoclave lined with Teflon® and subjected to a hydrothermal treatment at 110° C. for 14 hours under stirring. Pressure in the autoclave during the treatment was $1\times10^5$–$2\times10^5$ Pa. The suspension was subsequently taken out from the autoclave, centrifuged, washed with water, dried at 60° C., and a powdery catalytic composition (Pb—P) for comparison containing Pb and $PO_4$ was obtained.

(4) Preparation of a Comparative Catalyst [Sample (4)]

0.182 g of divanadium pentaoxide ($V_2O_5$) was dissolved in a 2M aqueous solution of sodium hydroxide (7 ml) prepared at room temperature. To this resultant solution, 0.789 g of calcium nitrate ($Ca(NO_3)_2.4H_2O$) dissolved in an 8 mL aqueous solution was added at room temperature to render the Ca/V ratio of 1.67, and a suspension was obtained.

The obtained suspension was introduced into an autoclave lined with Teflon® and subjected to a hydrothermal treatment at 110° C. for 14 hours under stirring. Pressure in the autoclave during the treatment was $1\times10^5$–$2\times10^5$ Pa. The suspension was subsequently taken out from the autoclave, centrifuged, washed with water, dried at 60° C., and a powdery catalytic composition (Ca—V) for comparison containing Ca and $PO_4$ was obtained.

(5) Preparation of a Comparative Catalyst [Sample (5)]

0.182 g of divanadium pentaoxide ($V_2O_5$) was dissolved in a 2M aqueous solution of sodium hydroxide (7 ml) prepared at room temperature. To this resultant solution, 0.706 g of strontium nitrate ($Sr(NO_3)_2$) dissolved in an 8 mL aqueous solution was added at room temperature to render the Sr/V ratio of 1.67, and a suspension was obtained.

The obtained suspension was introduced into an autoclave lined with Teflon® and subjected to a hydrothermal treatment at 110° C. for 14 hours under stirring. Pressure in the autoclave during the treatment was $1 \times 10^5 - 2 \times 10^5$ Pa. The suspension was subsequently taken out from the autoclave, centrifuged, washed with water, dried at 60° C., and a powdery catalytic composition (Sr—V) for comparison containing Sr and $PO_4$ was obtained.

(6) Preparation of a Comparative Catalyst [Sample (6)]

0.182 g of divanadium pentaoxide ($V_2O_5$) was dissolved in a 2M aqueous solution of sodium hydroxide (7 ml) prepared at room temperature. To this resultant solution, 1.105 g of lead nitrate ($Pb(NO_3)_2$) dissolved in an 8 mL aqueous solution was added at room temperature to render the Pb/V ratio of 1.67, and a suspension was obtained.

The obtained suspension was introduced into an autoclave lined with Teflon® and subjected to a hydrothermal treatment at 110° C. for 14 hours under stirring. Pressure in the autoclave during the treatment was $1 \times 10^5 - 2 \times 10^5$ Pa. The suspension was subsequently taken out from the autoclave, centrifuged, washed with water, dried at 60° C., and a powdery catalytic composition (Pb—V) for comparison containing Pb and $VO_4$ was obtained.

(7) Preparation of a Comparative Catalyst [Sample (7)]

Sample (7) which is a comparative catalyst is a hydrotalcite compound having the 4HTC:Mg/Al ratio of 4/1.

To a mixed aqueous solution (50 mL) of a 7M aqueous solution of sodium hydroxide and a 2M aqueous solution of sodium carbonate prepared at room temperature, a mixed aqueous solution (50 mL) of 4M magnesium nitrate ($Mg(NO_3)_2$) and 1M aluminum nitrate ($Al(NO_3)_2$) was admixed at room temperature under stirring. The obtained suspension was left to rest at 60° C. for 12 hours. Subsequently, the suspension was centrifuged, washed with water, dried at 60° C., and a powdery catalytic composition (4HTC) for comparison with the Mg/Al ratio of 4 and having a hydrotalcite structure was obtained.

(8) Commercially Available Magnesium Oxide (MgO) was Provided as a Comparative Catalyst [Sample (8)].

(9) Commercially Available Calcium Hydroxide ($Ca(OH)_2$) was Provided as a Comparative Catalyst [Sample (9)].

(Preparation of Catalysts Using Varied Concentrations of the Aqueous Solution of Sodium Hydroxide (NaOH) for Synthesis)

(10) Preparation of a Catalyst of the Present Invention [Sample (10)]

Sample (10) was prepared in the same manner as in the preparation method for Sample (2) except that the concentration of the aqueous solution of sodium hydroxide (7 mL) for use was varied from 1M to 1.143M.

(11) Preparation of a Catalyst of the Present Invention [Sample (11)]

Sample (11) was prepared in the same manner as in the preparation method for Sample (2) except that the concentration of the aqueous solution of sodium hydroxide (7 mL) for use was varied from 1M to 2M.

(12) Preparation of a Catalyst of the Present Invention [Sample (12)]

Sample (12) was prepared in the same manner as in the preparation method for Sample (2) except that the concentration of the aqueous solution of sodium hydroxide (7 mL) for use was varied from 1M to 4M.

(Preparation of Catalysts Using Varied Temperatures for Hydrothermal Treatment During Synthesis)

(13) Preparation of a Catalyst of the Present Invention [Sample (13)]

Sample (13) was prepared in the same manner as in the preparation method for Sample (2) except that the temperature for the hydrothermal treatment was varied from 110° C. to 150° C.

(14) Preparation of a Catalyst of the Present Invention [Sample (14)]

Sample (14) was prepared in the same manner as in the preparation method for Sample (2) except that the temperature for the hydrothermal treatment was varied from 110° C. to 200° C.

(15) Preparation of a Catalyst of the Present Invention [Sample (15)]

Sample (15) was prepared in the same manner as in the preparation method for Sample (2) except that the temperature for the hydrothermal treatment was varied from 110° C. to 220° C.

(Preparation of Catalysts Using Varied Concentrations of the Aqueous Solution of Sodium Hydroxide and Varied Temperatures for Hydrothermal Treatment During Synthesis)

(16) Preparation of a Catalyst of the Present Invention [Sample (16)]

Sample (16) was prepared in the same manner as in the preparation method for Sample (2) except that the concentration of the aqueous solution of sodium hydroxide (7 mL) for use was varied from 1M to 2M and the temperature for the hydrothermal treatment was varied from 110° C. to 50° C.

(17) Preparation of a Catalyst of the Present Invention [Sample (17)]

Sample (17) was prepared in the same manner as in the preparation method for Sample (2) except that the concentration of the aqueous solution of sodium hydroxide (7 mL) for use was varied from 1M to 2M and the temperature for the hydrothermal treatment was varied from 110° C. to 150° C.

(Preparation of Catalysts Using Varied Types and Concentrations of Alkali for Synthesis)

(18) Preparation of a Catalyst of the Present Invention [Sample (18)]

Sample (18) was prepared in the same manner as in the preparation method for Sample (2) except that the aqueous solution of sodium hydroxide (7 mL) for use was varied to an aqueous solution of potassium hydroxide (KOH) and the concentration was varied from 1M to 2M.

(19) Preparation of a Catalyst of the Present Invention [Sample (19)]

Sample (19) was prepared in the same manner as in the preparation method for Sample (2) except that the aqueous solution of sodium hydroxide (7 mL) for use was varied to an aqueous solution of ammonia ($NH_3$) and the concentration was varied from 1M to 2M.

(20) Preparation of a Catalyst of the Present Invention [Sample (20)]

Sample (20) was prepared in the same manner as in the preparation method for Sample (2) except that the aqueous solution of sodium hydroxide (7 mL) for use was varied to an aqueous solution of lithium hydroxide (LiOH) and the concentration was varied from 1M to 2M.

(21) Preparation of a Catalyst of the Present Invention [Sample (21)]

Sample (21) was prepared in the same manner as in the preparation method for Sample (2) except that the aqueous solution of sodium hydroxide (7 mL) for use was varied to an aqueous solution of rubidium hydroxide (RbOH) and the concentration was varied from 1M to 2M.

Example 1

Fine powders of the above Samples (1) to (9) were molded into plate-like pellets of 250-500 µm. 0.5 g of the molded substance (catalyst) was filled in a glass tube (50 cm length, 10 mm diameter) and heated (dehydrated) as a pretreatment at 550° C. for 3 hours under a carrier gas atmosphere (Ar: Flow rate was 30 mL/min). Upon completion of the heating (dehydration) treatment, reaction was conducted at normal pressure under the conditions of 300° C. reaction temperature, 1.5 mol % ethanol concentration (partial pressure of ethanol=1.56 kPa), and 30 mL/min flow rate for the carrier gas. The reaction time was set for 2 hours.

A gas chromatography mass spectrometer (GC-MS, measurement conditions are as shown below) was used for identifying components of the reactant gas, and gas chromatography (GC, measurement conditions are as shown below) was used for measuring the conversion rate of ethanol and selectivity of the reactant gas (Detector: FID). Calculation was conducted based on the peak area of each component by using the following formulae.

Butanol yield($C$-%)=100×($GC$ area of butanol)/($GC$ area of ethanol gas before reaction)

Butanol selectivity($C$-%)=100×($GC$ area of butanol)/(total $GC$ area of product)

Ethanol conversion rate($C$-%)=100×(total $GC$ area of product)/($GC$ area of ethanol gas before reaction)

Results (yield and selectivity of butanol using various catalysts) are shown in Table 1. In Table 1, Sr—P in Sample (2) is strontium phosphate apatite, a major component of a catalyst of the present invention for synthesizing butanol.

W/F (Catalyst weight (g)/Ethanol flow rate (g/hr)) in Example 1 is 8.8 hours.

(1) Gas Chromatography Equipped with a Flame Ionization Detector (GC-FID)

Reaction products were analyzed using GC-14B (Shimadzu Corporation). DB-WAX was used as a column. $N_2$ was used as a carrier gas and the pressure was set at 100 kPa. Analysis conditions are as follows.

Injection temperature: 250° C.
Detector temperature: 200° C.
Oven temperature: 50° C. (5 min)→5° C./min→200° C. (5 min)

(2) Gas Chromatography Equipped with Mass Spectrometric Detector (GC-MS)

Reaction products were analyzed using HP5890 (GC) and HP5972 (MSD) (Hewlett-Packard Development Company, L.P.). DB-624 was used as a column. High-purity helium (He) was used as a carrier gas and flow rate was set at 2.34 mL/min.

The analysis conditions were as follows.
Injection temperature: 250° C.
Detector temperature: 250° C.
Oven temperature: 40° C. (5 min)→10° C./min→240° C. (5 min)

(Discussion on the Results of Example 1)

The following findings are demonstrated in Table 1 that shows results of the reactions conducted under the conditions described above by using as a catalyst various apatite compounds prepared as above (Ca—P, Sr—P, Pb—P, Ca—V, Sr—V and Pb—V) and a Mg—Al series hydrotalcite (4HTC: Mg/Al=4), as well as commercially available catalysts, Ca(OH)$_2$ and MgO.

Yield and selectivity of butanol are dependent on the constitutional elements of an apatite catalyst, and high yield and selectivity were observed for Ca—P and Sr—P catalysts. These catalysts have both acid catalysis sites and base catalysis sites, both of which are considered to be relatively weak. For this reason, it is thought that a catalyst having relatively weak acid sites and basic sites is suitable to synthesize butanol from ethanol. Since butanol was also formed with a Mg—Al series hydrotalcite (4HTC) that is said to have both acid and basic sites, it is suggested that functions of both acid and base are necessary. Among these, strontium phosphate apatite (Sr—P), the major component of a catalyst of the present invention, has been shown to have the highest butanol selectivity.

Example 2

Using a molded form (catalyst) of strontium phosphate apatite (a major component of a catalyst of the present invention) of Sample (2), the conversion rate of ethanol (partial pressure=1.56 kPa) was varied by changing the catalyst quantity (0.5-2.0 g) and flow rate (30-60 mL/min) in Example 1. Then, distribution of the products was observed. The reaction time was set for 2 hours.

The results are shown in Table 2.

(Discussion on the Results of Example 2)

The more the conversion rate is increased, the more the selectivity of acetaldehyde and 2-buten-1-ol is decreased. On the other hand, selectivity of butylaldehyde and alcohol of $C_6$ or more is increased. The selectivity of butanol was initially increased as the contact time increased, but then the selectivity decreased. Further, crotonaldehyde was detected in very minute amounts only at the early stage of the reaction.

These results suggests that it is a reaction mechanism routing through an aldol reaction as shown in FIG. 1 (Guerbet reaction: [1]). "No entry sign" in FIG. 1 denotes a reaction that hardly occurs.

The indication [2] in FIG. 1 denotes a reaction formula in which higher alcohol is formed from butanol. As shown in FIG. 1, acetaldehyde is formed in the first place by a dehydrogenation reaction of ethanol. Next, the formed acetaldehyde undergoes an aldol condensation and crotonaldehyde is formed via dehydration of aldol. Since formation of aldol and crotonaldehyde are basically not observed under any condition, these are thought to be unstable and to exist as intermediates and thought to immediately undergo dehydration and hydrogenation. There are two hydrogenation sites, at the double bonding and at the carbonyl group, but it is likely that the reaction proceeds via 2-buten-1-ol, since 2-buten-1-ol is often observed under conditions where the conversion rate is low. Butanol is then formed by hydrogenation of 2-buten-1-ol. Butylaldehyde is thought to be formed by a dehydrogenation reaction (consecutive reaction) of butanol, and not to be involved in butanol formation, but rather an intermediate of a reaction to obtain alcohol of more than $C_6$ from butanol.

It is thought that the acid sites of apatite act on dehydration reactions and the basic sites act on dehydrogenation reactions and aldol condensation.

Example 3

Figure 2:
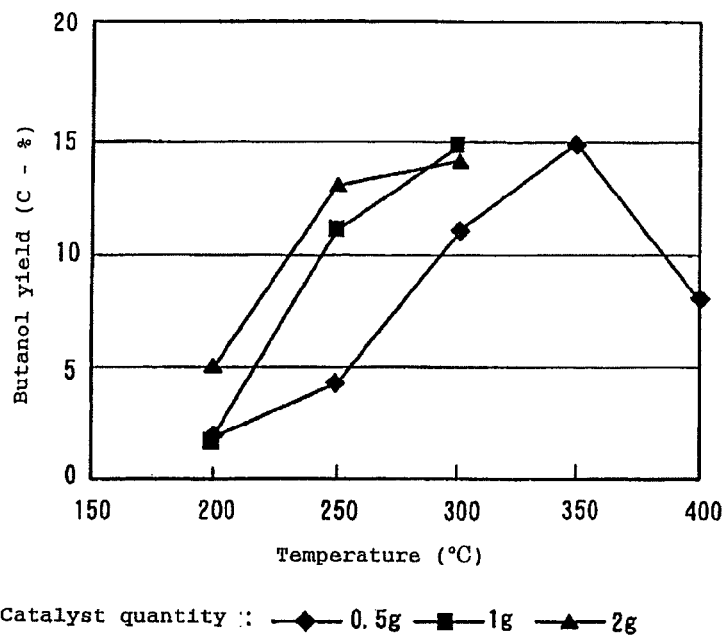
FIG. 2 is a graph showing temperature dependency of the butanol yield in a reaction using a strontium phosphate apatite catalyst.
Figure 3:
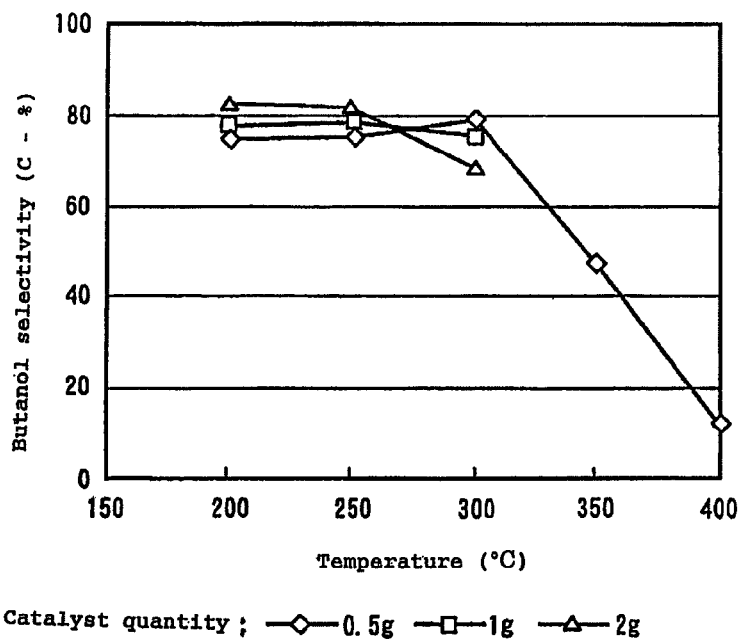
FIG. 3 is a graph showing temperature dependency of the butanol selectivity in a reaction using a strontium phosphate apatite catalyst.

Using a molded form of strontium phosphate apatite of Sample (2), the catalyst quantity and temperature were varied under the same conditions as in Example 1, and the yield and the selectivity of n-butanol were monitored. The results are shown in FIGS. 2 and 3.

(Discussion on the Results of Example 3)

In order to further improve the yield and selectivity of butanol, the Sr—P catalyst was used and an attempt made to optimize the reaction conditions by varying the reaction temperature and catalyst quantity. According to FIGS. 2 and 3, which show changes in yield and selectivity of butanol, the yield of butanol is increased as the reaction temperature is increased when the catalyst quantity is 0.5 g and about 15 C-% is achieved at 350° C., but the yield is conversely decreased at 400° C. The selectivity is also increased as the temperature is increased and about 80 C-% was achieved at 300° C., but is decreased at 350° C. or higher due to side reactions or consecutive reactions. At the reaction temperature of 250° C., the butanol yield is improved as the catalyst quantity is increased, and the selectivity is also increased similarly. On the other hand, at the reaction temperature of 300° C., the yield is almost the same for the 1 g sample as for the 2 g sample, and the selectivity is decreased as the catalyst quantity is increased.

Further, the higher the reaction temperature, the more the conversion of ethanol proceeds and the faster the formation rate of butanol is. At the same time, however, consecutive reactions (formation of higher alcohols, etc.) or side reactions (formation of ethylene, etc.) also increase. For this reason, temperature within the range of 250-300° C. is thought to be the optimum in order to obtain butanol at a high selectivity. On the other hand, since the influence of the catalyst quantity is similar to that of the reaction temperature, a catalyst quantity of 2 g is thought to be suitable at the reaction temperature of 250° C. and a catalyst quantity of 1 g at the reaction temperature of 300° C. Further, the butanol yield hits a peak at about 15 C-%, even when the conditions are varied. This is probably because the formed butanol is undergoing a consecutive reaction. Since a consecutive reaction is a competitive reaction that uses ethanol as a raw material, it is thought that the yield of butanol can be increased by increasing the concentration of ethanol introduced. As a result of the above consideration, butanol yield of 15 C-% and selectivity of 75 C-% are achieved under the conditions of 300° C. reaction temperature and 1 g catalyst quantity.

Example 4

Fine powders of the above Samples (1), (2) and (10) to (21) were molded into plate-like pellets of 250-500 μm. 2.0 g of the molded substance was placed in a glass tube (50 cm length, 10 mm diameter) and heated (dehydrated) as a pre-treatment at 550° C. for 3 hours under a carrier gas atmosphere (He: Flow rate 30 mL/min). Upon completion of the heating (dehydration) treatment, reaction was conducted at normal pressure under the conditions of 300° C. reaction temperature, 16.1 mol % ethanol concentration, and 30 mL/min flow rate for the carrier gas (He).

Here, W/F (Catalyst weight (g)/Ethanol flow rate (g/hr)) is 2.8 hours. Other analysis conditions and methods are the same as in Example 1.

For Sample (19), reaction was conducted under the conditions of 16.1 mol % ethanol concentration, 20 mL/min flow rate for the carrier gas, and W/F (Catalyst weight (g)/Ethanol flow rate (g/hr)) being 4.2 hours.

Further, for Sample (20), reaction was conducted under the conditions of 16.1 mol % ethanol concentration, 10 mL/min flow rate for the carrier gas, and W/F (Catalyst weight (g)/Ethanol flow rate (g/hr)) being 8.4 hours.

The catalyst types, preparation conditions, reaction conditions, and the results are shown in Table 3 below.

The reaction conditions in Table 3 are as follows.
1) Catalyst quantity: 2.0 g, temperature: 300° C., ethanol concentration: 16.1 vol-% (He balance), total flow rate: 35.8 mL/min, W/F=2.8 h, reaction time: 3 hr
2) Catalyst quantity: 2.0 g, temperature: 300° C., ethanol concentration: 16.1 vol-% (He balance), total flow rate: 23.8 mL/min, W/F=4.2 hr, reaction time: 3 hr
3) Catalyst quantity: 2.0 g, temperature: 300° C., ethanol concentration: 16.1 vol-% (He balance), total flow rate: 11.9 mL/min, W/F=8.4 hr, reaction time: 3 hr (Discussion on the Results of Example 4)

The results shown in Table 3 confirmed the following.

The alkali amount when preparing the Sr—P apatite catalyst [Sample (2)] which is the fundamental catalyst, the temperature for hydrothermal treatment, and the alkali types were varied. In all cases, however, it was possible to obtain butanol, the desired product, at a higher selectivity than when the Ca—P apatite catalyst for comparison [Sample (1)] was used.

The butanol yield was inferior to that obtained when the Ca—P apatite catalyst [Sample (1)] was used, but this is not a problem because unreacted substances can be recycled at the time of industrialization, and catalysts of Samples (10) to (21), having a selectivity that is higher by as much as about 9-16%, are very superior catalysts with fewer by-products.

The following reagents were used in the Examples and Comparative Examples.

<For Sample Preparation (Production of Apatite Solid Solution, Etc.)>

$Ca(NO_3)_2.4H_2O$: Purity 98.5% [first-class reagent, Wako Pure Chemical Industries, Ltd.]

$Sr(NO_3)_2$: Purity 98.0% [first-class reagent, Wako Pure Chemical Industries, Ltd.]

$Pb(NO_3)_2$: Purity 99.5% [first-class reagent, Wako Pure Chemical Industries, Ltd.]

$Al(NO_3)_3.9H_2O$: Purity 98.0% [first-class reagent, Wako Pure Chemical Industries, Ltd.]

$Mg(NO_3)_2.6H_2O$: Purity 99.5% [first-class reagent, Wako Pure Chemical Industries, Ltd.]

$V_2O_5$: Purity 99.0% [first-class reagent, Wako Pure Chemical Industries, Ltd.]

$P_2O_5$: Purity 98.0% [first-class reagent, Wako Pure Chemical Industries, Ltd.]

$(NH_4)_2HPO_4$: Purity 99.0% [first-class reagent, Wako Pure Chemical Industries, Ltd.]

$NH_4F$: Purity 97.0% [first-class reagent, Wako Pure Chemical Industries, Ltd.]

NaOH: Purity 97.0% [first-class reagent, Wako Pure Chemical Industries, Ltd.]

$NH_3$ water (25% by mass): Purity 25.0% [first-class reagent, Wako Pure Chemical Industries, Ltd.]

$Ca(OH)_2$: Purity 96.0% [first-class reagent, Wako Pure Chemical Industries, Ltd.]

High-purity microfine magnesia (MgO): [Ube Material Industries, Ltd.]

<Gas Chromatography>

Helium (He): TOSA SANSO K.K.

Ar: TOSA SANSO K.K.

$H_2$: TOSA SANSO K.K.

$N_2$: TOSA SANSO K.K.

High purity He: TAIYO NIPPON SANSO CORPORATION

<Synthesis of Butanol from Ethanol>

Ethanol (dehydrated): Purity 99.5% [For organic synthesis, Wako Pure Chemical Industries, Ltd.]
Ar: TOSA SANSO K.K.

TABLE 1

| Catalyst type | | Ethanol conversion rate (%) | Butanol yield (C-%) | Butanol selectivity (C-%) |
|---|---|---|---|---|
| Sample (1) | Ca—P | 18.1 | 11.9 | 66.0 |
| Sample (2) | Sr—P | 14.1 | 11.1 | 79.2 |
| Sample (3) | Pb—P | 6.4 | 0.0 | 0.0 |
| Sample (4) | Ca—V | 20.8 | 3.1 | 14.6 |
| Sample (5) | Sr—V | 7.1 | 0.2 | 3.2 |
| Sample (6) | Pb—V | 5.4 | 0.0 | 0.0 |
| Sample (7) | 4HTC | 14.1 | 7.0 | 49.3 |
| Sample (8) | MgO | 0.9 | 0.0 | 0.0 |
| Sample (9) | Ca(OH)$_2$ | 0.9 | 0.0 | 0.0 |

TABLE 2

| Ethanol conversion rate (%) | Selectivity of each product (C-%) | | | | | | |
|---|---|---|---|---|---|---|---|
| | $CH_3CHO$ | $C_3H_5CHO$ | 2-buten-1-ol | $C_3H_7CHO$ | n-butanol | Higher alcohols | Others |
| 2.7 | 15.5 | 0.0 | 5.9 | 0.0 | 64.5 | 5.8 | 8.4 |
| 7.2 | 5.5 | 0.0 | 2.0 | 0.5 | 73.6 | 8.7 | 9.7 |
| 13.9 | 3.0 | 0.0 | 1.4 | 0.7 | 76.5 | 10.4 | 8.0 |
| 20.5 | 1.8 | 0.0 | 0.0 | 2.2 | 68.9 | 13.7 | 13.4 |

TABLE 3

| | Catalyst type and treatment condition | Preparation conditions for catalyst | | | | Reaction results | | | Reaction conditions |
|---|---|---|---|---|---|---|---|---|---|
| | | Sr/P ratio | Alkali type | Alkali quantity (mmol) | Hydrothermal treatment temperature (° C.) | Ethanol conversion rate (%) | Butanol yield (C-%) | Butanol selectivity (C-%) | |
| Sample (1) | Catalyst for comparison [Ca—P apatite] | — | NaOH | 7 | 110 | 21.1 | 14.8 | 70.1 | *1) |
| Sample (2) | Fundamental catalyst [Sr—P apatite] | 1.68 | NaOH | 7 | 110 | 9.9 | 8.1 | 81.5 | *1) |
| Sample (10) | Varying alkali quantity | 1.68 | NaOH | 8 | 110 | 10.4 | 8.5 | 83.1 | *1) |
| Sample (11) | Varying alkali quantity | 1.70 | NaOH | 14 | 110 | 10.2 | 8.8 | 86.1 | *1) |
| Sample (12) | Varying alkali quantity | 1.69 | NaOH | 28 | 110 | 13.2 | 10.7 | 81.1 | *1) |
| Sample (13) | Varying hydrothermal treatment temperature | 1.69 | NaOH | 7 | 150 | 9.9 | 8.4 | 85.3 | *1) |
| Sample (14) | Varying hydrothermal treatment temperature | 1.66 | NaOH | 7 | 200 | 9.4 | 7.7 | 82.1 | *1) |
| Sample (15) | Varying hydrothermal treatment temperature | 1.75 | NaOH | 7 | 220 | 7.9 | 6.8 | 85.6 | *1) |
| Sample (16) | Varying alkali quantity + hydrothermal treatment temperature | 1.63 | NaOH | 14 | 50 | 15.4 | 12.6 | 81.5 | *1) |
| Sample (17) | Varying alkali quantity + hydrothermal treatment temperature | 1.69 | NaOH | 14 | 150 | 9.7 | 8.1 | 83.7 | *1) |
| Sample (18) | Varying alkali type + alkali quantity | 1.74 | KOH | 14 | 110 | 11.5 | 9.8 | 85.1 | *1) |
| Sample (19) | Varying alkali type + alkali quantity | 1.71 | $NH_3$ | 14 | 110 | 10.0 | 7.9 | 79.0 | *2) |
| Sample (20) | Varying alkali type + alkali quantity | 1.69 | LiOH | 14 | 110 | 12.4 | 9.9 | 79.5 | *3) |
| Sample (21) | Varying alkali type + alkali quantity | 1.98 | RbOH | 14 | 110 | 8.1 | 6.4 | 79.3 | *1) |

INDUSTRIAL APPLICABILITY

A method using the catalyst of the present invention enables synthesis of butanol from ethanol at a high selectivity, and the method can be effectively used in the field of biofuels and the like.

The invention claimed is:

1. An alcohol synthesis method for synthesizing butanol from ethanol, wherein the method comprises a step of contacting ethanol with a catalyst comprising strontium phosphate apatite having a Sr/P atomic ratio of 1.5-2.0.

2. An alcohol synthesis method, wherein the method comprises a step of sequentially or intermittently removing to the outside of a reaction system at least butanol from a reaction product obtained by contacting ethanol with a catalyst comprising strontium phosphate apatite having a Sr/P atomic ratio of 1.5-2.0, and comprising butanol as a major component.

3. The alcohol synthesis method according to claim 1, wherein ethanol is contacted with the catalyst at 200-350° C.

4. The alcohol synthesis method according to claim 1, wherein ethanol is produced using biomass as a material and the water content of the ethanol is 10% or less.

5. The alcohol synthesis method according to claim 2, wherein ethanol is contacted with the catalyst at 200-350° C.

6. The alcohol synthesis method according to claim 2, wherein ethanol is produced using biomass as a material and the water content of the ethanol is 10% or less.

7. An alcohol synthesis method for synthesizing butanol from ethanol, wherein the method comprises a step of contacting ethanol with a catalyst comprising strontium phosphate apatite.

8. An alcohol synthesis method, wherein the method comprises a step of sequentially or intermittently removing to the outside of a reaction system at least butanol from a reaction product obtained by contacting ethanol with a catalyst comprising strontium phosphate apatite, and comprising butanol as a major component.

9. The alcohol synthesis method according to claim 7 or 8, wherein ethanol is contacted with the catalyst at 200-350° C.

10. The alcohol synthesis method according to claim 7 or 8, wherein ethanol is produced using biomass as a material and the water content of the ethanol is 10% or less.

* * * * *